United States Patent [19]

Siegal

[11] Patent Number: 5,062,156

[45] Date of Patent: Nov. 5, 1991

[54] FACE SHIELD FILTER PLATE RETENTION

[75] Inventor: Burton L. Siegal, Skokie, Ill.

[73] Assignee: Sellstrom Manufacturing Company, Palatine, Ill.

[21] Appl. No.: 624,493

[22] Filed: Dec. 6, 1990

Related U.S. Application Data

[63] Continuation of Ser. No. 451,423, Dec. 15, 1989, abandoned.

[51] Int. Cl.$^5$ ............................................... A61F 9/06
[52] U.S. Cl. ............................................................ 2/8
[58] Field of Search ...................... 2/7, 8, 15, 424, 431, 2/434

[56] References Cited

U.S. PATENT DOCUMENTS

| | | | |
|---|---|---|---|
| 1,508,907 | 9/1924 | Work | 2/11 |
| 1,795,866 | 3/1931 | King | 2/8 |
| 3,056,140 | 10/1962 | Lindblom | 2/434 |
| 3,257,667 | 6/1966 | Anderson | 2/8 |
| 3,444,561 | 5/1969 | Boyer | 2/8 |
| 3,577,563 | 5/1971 | Raschke | 2/8 |
| 4,774,723 | 10/1988 | Ruck | 2/8 |

Primary Examiner—Werner H. Schroeder
Assistant Examiner—Michael A. Neas
Attorney, Agent, or Firm—Neuman, Williams, Anderson & Olson

[57] ABSTRACT

In face-protecting devices such as welder's shields and helmets, a filter plate is supported on a support ledge adjacent the view port and is retained on the exterior of the device by a filter plate retainer adapted for attachment to the device.

13 Claims, 2 Drawing Sheets

FACE SHIELD FILTER PLATE RETENTION

This application is a continuation of application No. 451,423 filed Dec. 15, 1989, now abandoned.

This invention relates to face-protecting devices of the type utilized by welders and more particularly to improvements in retaining filter plates in the viewing ports thereof.

BACKGROUND OF THE INVENTION

Welders and others wear shields or helmets to protect their faces and eyes from infrared, ultra-violet and part of the visible light emanating from the work area. To this end, the shields are provided with a viewing port which holds an eye-protecting light filter screen of a translucent material to filter light rays, particularly ultra-violet and infrared rays. Usually a relatively inexpensive clear glass or plastic is placed over the light filtering screen to protect the filter from flying sparks and molten metal such as encountered in welding.

Filter plate as used herein encompasses both panes of material, the one that filters radiation and the overlying protective glass or plastic plate which is generally used to protect the filter. Prior art filter plate holders are generally inserted into the welder's shield or helmet from the rear or interior by snap action and generally involve a mechanism whereby the filter plates are held against the inside of the helmet surface by spring retainer means.

Recent industry safety regulations impose more stringent requirements on eye-protecting devices such as welder's shields or helmets and require that they meet certain standards, particularly with respect to increased impact resistance. Filter plate holders which are inserted in shields or helmets from inside the helmet and held against the interior surface of the shield often do not meet the more stringent standards with respect to impact resistance.

OBJECTS OF THE INVENTION

It is thus a principal object of this invention to provide improvements in the eye-pieces of face-protecting devices such as welder's face shields, helmets and the like.

It is a more specific object of the invention to provide novel and advantageous improvements in retaining filter plates in face-protecting devices such as welder's shields, helmets and the like.

It is a further object of the invention to provide a filter plate retainer for face-protecting devices such as welder's shields, helmets and the like which is attached to the face-protecting device from the outside.

It is a still further object of this invention to provide a filter plate retainer for face-protecting devices such as welder's shields, helmets and the like which affords good impact resistance.

SUMMARY OF THE INVENTION

The present invention provides means for retaining filter plates over the view port of a face-protecting device whereby the filter plates are supported on the exterior of the face-protecting device by a recessed support ledge and retained in position by a filter plate retainer having fastening mean for attachment to the face protecting device.

In one presently preferred embodiment, the present invention involves a filter plate retainer for use with face-protecting devices having a viewing port therein surrounded by a slotted recessed support ledge. The retainer comprises an integral flexible frame of a size and shape to surround the viewing port. The frame is provided with fastening means for attachment to the face-protecting device from the exterior thereof. The retainer is attached to the exterior of the face-protecting device over the filter plates. The retainer is adapted for use with face shields in general having a recessed support ledge surrounding the viewing port and provided with means to receive the fastening means provided on the retainer.

DESCRIPTION OF PREFERRED EMBODIMENTS

Figure 1:
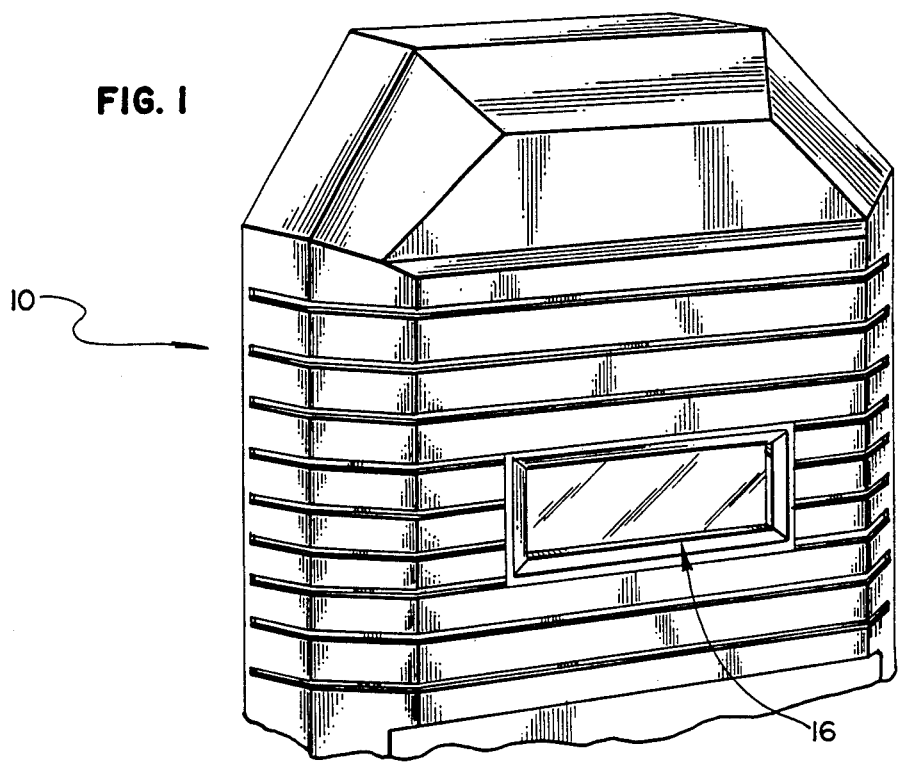
FIG. 1 is a perspective partial view of a typical face-protecting device such as a welder's shield or helmet with the filter plate retainer of the invention attached in place.
Figure 2:
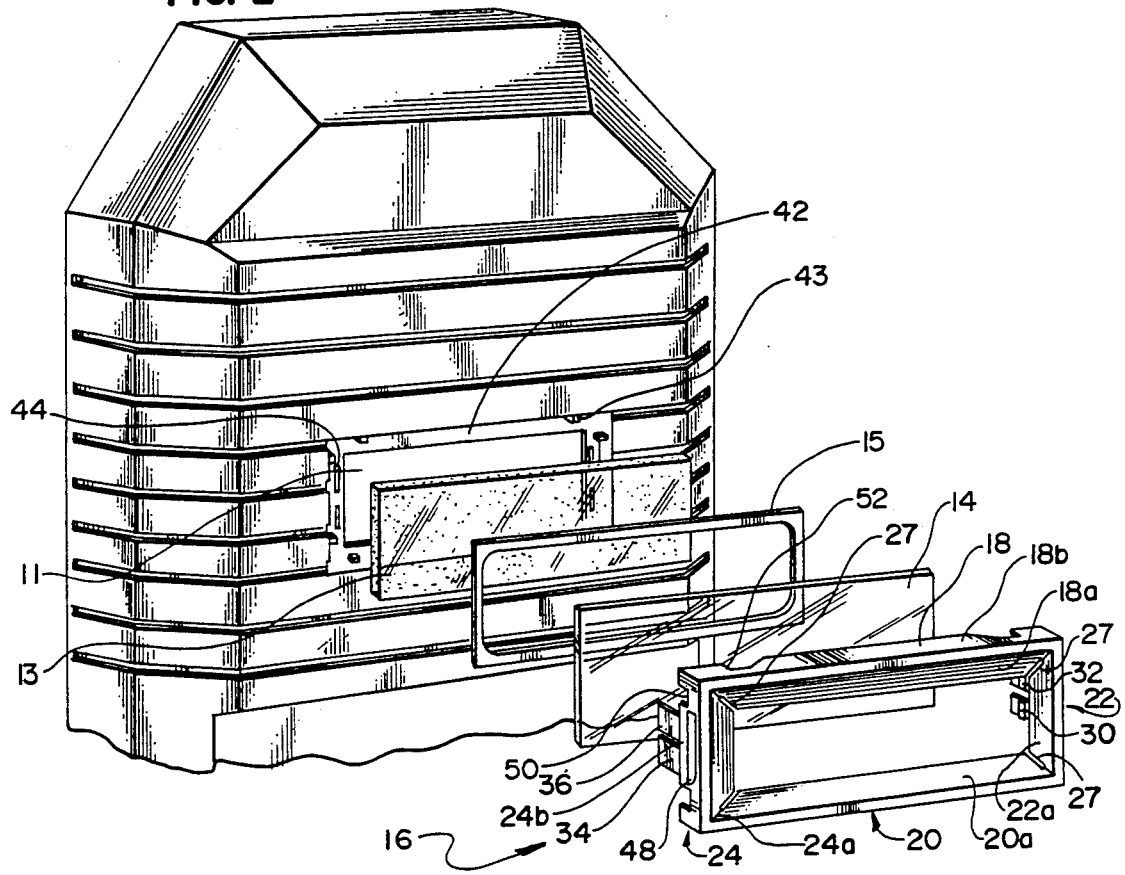
FIG. 2 is a view similar to FIG. 1 showing the method of assembling the filter plates and plate retainer for attachment to the device.
Figure 3:
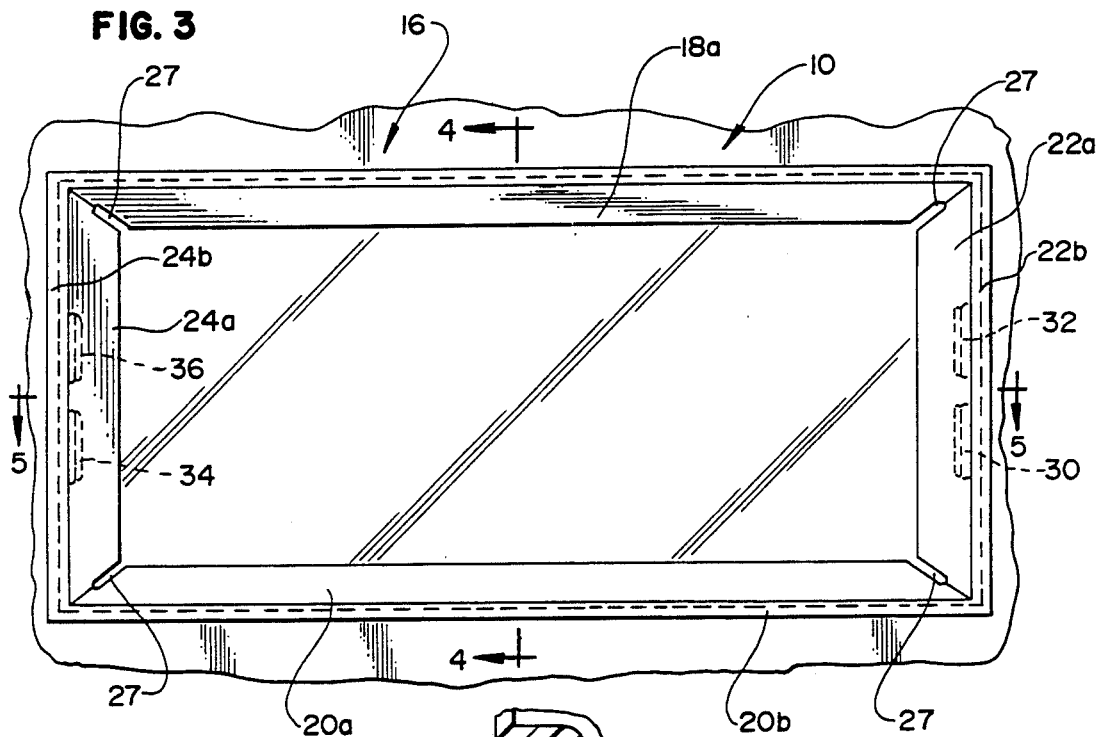
FIG. 3 is a plan view of a plate retainer in accordance with this invention.
Figure 4:
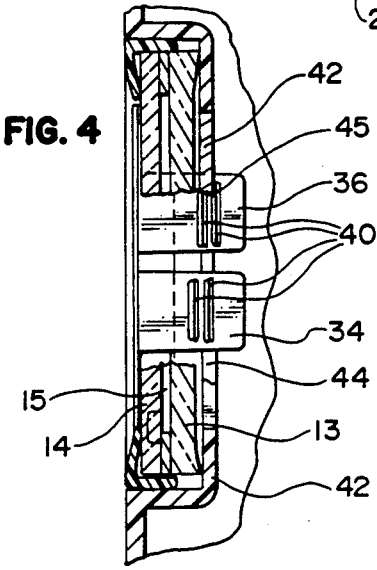
FIG. 4 is a view taken on the line 4—4 of FIG. 3.
Figure 5:
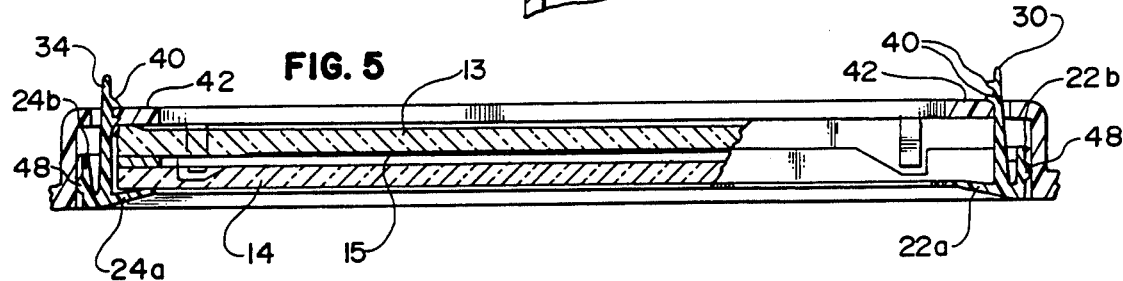
FIG. 5 is a view taken on the line 5—5 of FIG. 3.

The filter plate retainer of this invention is adapted for exterior attachment to a face-protecting device such as a welder's shield or helmet, a typical device being designated by the numeral 10. Such devices have a view port 11 over which one or more filter plates 13 and 14 are placed. Usually a gasket 15 is employed between the plates.

According to one presently preferred embodiment, the plate retainer comprises a generally rectangular flexible frame 16 formed of L-shaped flanged top 18, bottom 20 and sides members 22 and 24 which form an integral unit. The retainer is formed of a sturdy, non-flammable, heat resistant material such as glass-filled nylon or the like. The size of the retainer will vary according to the size and shape of the viewing port of the welder's shield which are typically rectangular in shape and 2"×4¼" or 3"×5¼" or 4½"×5¾" in size. The retainer can be readily formed by known procedures, such as injection molding.

In one preferred form, the outer peripheral facing surfaces of the top, bottom and side members of the frame member are bevelled inwardly as at 18a, 20a, 22a and 24a so as to create an attractive picture frame effect. The top, bottom and sides of the frame function as cantilever spring-like elements to resiliently grip the filter plates. Four notches 27 are provided, preferably at each corner of the frame, which permit the said frame members to more freely flex.

The frame is also provided with inwardly projecting perimeter flanges 18b, 20b, 22b and 24b. These perimeter flanges surround the edges of the stack of filter plates 13 and 14 and gasket 15 (if used) and maintain the plates in alignment. These perimeter flanges project inwardly a distance less than the thickness of the stack of filter plates to be retained. In addition to holding the filter plates in alignment and providing support to the frame, the perimeter flanges also function as a barrier to light rays emanating from welding activity.

As shown in the drawings, closely adjacent to each side 22 and 24 of the frame 16 are fastening means comprising two spaced planarly aligned locking fingers designated by the numerals 30, 32, 34 and 36 which extend inwardly in a plane generally normal to the frame. One or more gripping barbs 40 are provided on either the interior or exterior surfaces of each of the locking fingers. The barbs on one locking finger are off-set, or not planarly aligned with the barbs on the planarly aligned adjacent locking finger so as to accommodate filter plate stacks of different thicknesses and to lock them snugly in the viewing port of the face-protecting device. Thus, the barbs 40 on locking finger 30 are non-planarly aligned with barbs 40 on the adjacent locking finger 32 and the same is true with the barbs on the adjacent locking fingers 34 and 36. In a less preferred embodiment, a single locking finger can be used on each side of the frame and with a desired number of relatively small finer barbs thereon. The use of two locking fingers carrying relatively larger barbs is preferred for better tolerance of abuse and better wear resistance. Other fastening means, such as, for example, rotary tab members adapted to pass through keyhole slots in the shield can be employed.

The plate retainer of this invention can be used with various face-protecting devices such as welder's shields or helmets and the like, such as, for example, as shown in U.S. Pat. Nos. 1,508,907, 3,257,667, 3,577,563 and others. The only modification of some such shields is that they be provided with a slotted recessed support ledge 42 around the periphery of the viewing port. If desired, such recessed support ledge 42 can be provided with spaced upstanding lugs 43 to serve as centering means for the innermost filter plate. The retainer frame is pushed in around the centering lugs 43. The face-protecting device should also be provided with slots 44 in the sides of the support ledge 42 to receive the gripping fingers 30, 32, 34 and 36 of the filter plate retainer.

In assembling the eye-protecting piece in the protective shield, a translucent light filter plate 13 is placed on the recessed support ledge 42 of the shield. Then, if desired, a gasket 15 is placed thereover followed by a protective glass or plastic plate 14. The retainer frame is then placed over the stack of filter plates with the locking fingers 30, 32, 34 and 36 being pushed through the slots 44 in the shield support ledge 42. Depending upon the thickness of the stack of filter plates, the flat surface of one of the barbs 40 on the locking fingers at each side of the frame will then engage the sharp edge 45 of the support ledge 42. The range of resilient grip of the frame will ideally be equal to or greater than the pitch or spacing between adjacent barbs.

The slots 44 in the shield support ledge 42 are preferably somewhat larger than the locking fingers for ease in engagement and disengagement which can be easily accomplished by laterally deflecting the flexible fingers to disengage the barbs from the edge of the support ledge. Because of the required clearance of slots 44, preferably a rub rail 48 is provided on the exterior of the inwardly projecting side flanges 22b and 24b of the frame so as to prevent the possibility of light entering the slots 44 when the eye-piece is assembled. The rub rails 48, by virtue of an interference fit press firmly against the side perimeter walls of the viewing port of the shield thus causing the rub rails' supporting flanges 22b and 24b to flex inwardly. By virtue of this inward flexure and the flexibility of the retainer frame itself, the locking fingers that carry the barbs press firmly against the edge of the slots in the shield support ledge. Notches 50 and 52 are preferably provided in the sides and top and bottom of the frame so as to accommodate and fit around lugs 43 on the support ledge of the face shield.

As will be appreciated, the filter plates are located on the outside of the face-protecting device and are firmly retained against a recessed support ledge surrounding the view port by the filter plate retainer of this invention. This insures that the filter plate exhibit good resistance to impact forces. Moreover, with the filter plate retainer of this invention, filter plates can easily be changed or inserted without the use of special tools. Filter plates, including a gasket between the plates, can be readily loaded into the view ports of a face-protecting device from the outside of the device and firmly retained by the retainer which is substantially flush with the face of the device.

Those modifications and equivalents which fall within the spirit of the invention are to be considered a part thereof.

What is claimed is:

1. In a face-protecting device having a viewing port therein, the improvement which comprises supporting a filter plate on a support ledge of a face-protecting device and retaining the filter plate on the exterior of said face-protecting device by a flexible filter plate retainer provided with integral fastening means projecting inwardly therefrom and means for adjustably engaging the fastening means with the face-protecting device.

2. A filter plate retainer for use with a face-protecting device having a viewing port therein with an adjacent support ledge, said retainer comprising an integral flexible frame of a size and shape to surround the viewing port, said frame carrying integral fastening means projecting inwardly therefrom and means for adjustably engaging the fastening means with the face protecting device.

3. A filter plate retainer according to claim 2 wherein said filter plate retainer is removable from the face-protecting device.

4. A filter plate retainer for use with face-protecting devices having a viewing port therein with an adjacent slotted recessed support ledge, said retainer comprising an integral frame of a size and shape to surround the viewing port and being provided with notches therein to facilitate flexing of the frame, at least one locking finger projecting inwardly and substantially normal to the frame adjacent to each side thereof, said locking finger carrying on a surface thereof at least one gripping barb.

5. A filter plate retainer according to claim 4 wherein said frame has bevelled outward facing exterior faces.

6. A filter plate retainer according to claim 4 wherein there are two spaced substantially planarly aligned locking fingers projecting inwardly and substantially normal to the frame adjacent distal sides thereof, each of said locking fingers carrying on a surface thereof at least one gripping barb, the barbs on one of said fingers being non-planarly aligned from the barbs on the other planarly aligned locking fingers.

7. A filter plate retainer according to claim 4 wherein the frame has intersecting flanged top, bottom and side members which are notched at the intersections thereof.

8. A filter plate retainer according to claim 4 wherein said filter plate retainer is removable from the face-protecting device.

9. In combination, a face-protecting device having a viewing port therein with an adjacent support ledge and a filter plate retainer comprising an integral flexible frame of a size and shape to surround the viewing port, said frame carrying integral fastening means projecting inwardly therefrom and means for adjustably engaging the fastening means with the face-protecting device.

10. The combination of claim 9 wherein the frame has intersecting flanged top, bottom and side members which are notched at the intersections thereof.

11. The combination of claim 9 wherein the support ledge is slotted and the filter plate retainer is provided with at least one locking fingers projecting inwardly and substantially normal to the frame adjacent each side thereof for engagement within said slotted support ledge, said locking fingers carrying on a surface thereof at least one gripping barb.

12. The combination of claim 9 wherein the filter plate retainer is provided with two spaced substantially planar aligned locking fingers projecting inwardly and substantially normal to the frame adjacent distal sides thereof for engagement within said slotted support ledge, each of said locking fingers carrying on a surface thereof at least one gripping barb, the barbs on one of said fingers being non-planarly aligned from the barbs on the other planarly aligned locking fingers.

13. The combination of claim 9 wherein said filter plate retainer is removable from the face-protecting device.

* * * * *